United States Patent [19]

Carlson et al.

[11] Patent Number: 4,646,273
[45] Date of Patent: Feb. 24, 1987

[54] METHOD AND APPARATUS FOR EVALUATING FLOW CHARACTERISTICS OF FLUID BEHIND PIPE

[75] Inventors: Norman R. Carlson, Houston; James M. Johnston, Santa Fe, both of Tex.

[73] Assignee: Dresser Industries, Inc., Dallas, Tex.

[21] Appl. No.: 779,180

[22] Filed: Sep. 23, 1985

Related U.S. Application Data

[63] Continuation of Ser. No. 436,235, Oct. 25, 1982, abandoned.

[51] Int. Cl.$^4$ .................... E21B 47/00; G01V 1/00
[52] U.S. Cl. .......................... 367/32; 73/155
[58] Field of Search ............... 73/40.5 A, 155, 861.18, 73/861.21, 861.27, 861.28, 861.29, 861.31, 24; 367/28, 30, 32, 34, 35, 86; 166/337, 264; 181/105

[56] References Cited

U.S. PATENT DOCUMENTS

| | | | |
|---|---|---|---|
| 3,784,828 | 1/1974 | Hayes | 250/106 |
| 4,046,220 | 9/1977 | Glenn, Jr. | 73/155 X |
| 4,114,721 | 9/1978 | Glenn, Jr. | 181/102 X |
| 4,173,718 | 11/1979 | Fertl | 250/259 |
| 4,217,659 | 8/1980 | Glenn, Jr. | 367/35 |
| 4,312,049 | 1/1982 | Masse et al. | 181/105 X |
| 4,319,346 | 3/1982 | MacDonald | 367/30 X |
| 4,328,567 | 5/1982 | Dodge | 367/49 X |
| 4,363,112 | 12/1982 | Widrow | 181/113 X |

OTHER PUBLICATIONS

Kermit Brown, The Technology of Artificial Lift Methods; vol. 1, Inflow Performance Multiphase Flow in Pipes, Penn Well Books, Tulsa, Oklahoma, (1977), p. 67.
Introduction to Sonar Logging, by F. O. Bohn-Dresser Dallas, Dresser Industries, Inc., Feb. 1979.

*Primary Examiner*—Charles T. Jordan
*Assistant Examiner*—Brian S. Steinberger
*Attorney, Agent, or Firm*—Patrick H. McCollum

[57] ABSTRACT

A method and system for well logging provide indications of the characteristics of fluid flow behind pipe. An acoustic listening device is positioned within a pipe in proximity to suspected fluid flow behind the pipe. Acoustic energy resulting from the fluid flow is detected and separated into at least two frequency groups or ranges; the first comprising acoustic energy of relatively low frequency and the second comprising acoustic energy of relatively higher frequency. The relative distribution of acoustic energy between the two frequency groups provides an indicator of the nature of the fluid flow behind the pipe.

4 Claims, 5 Drawing Figures

U.S. Patent  Feb. 24, 1987  Sheet 1 of 2  4,646,273
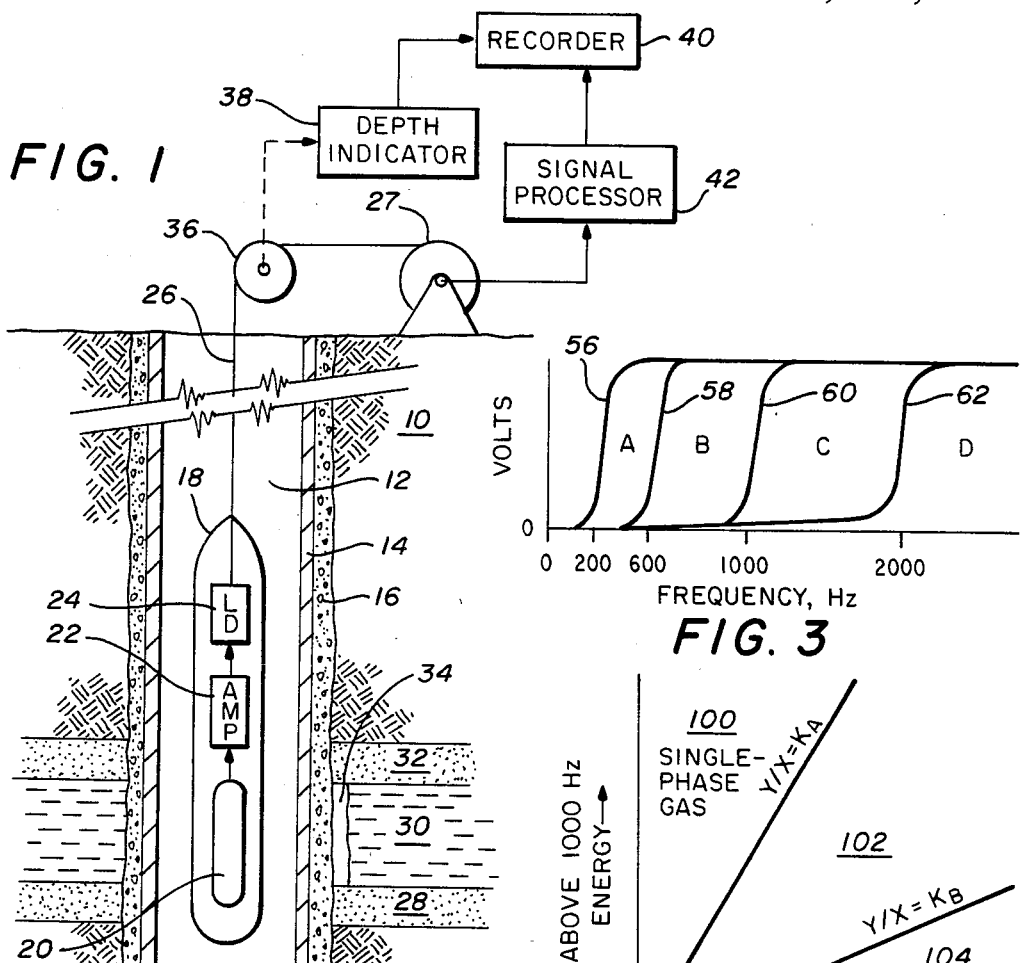
FIG. 1
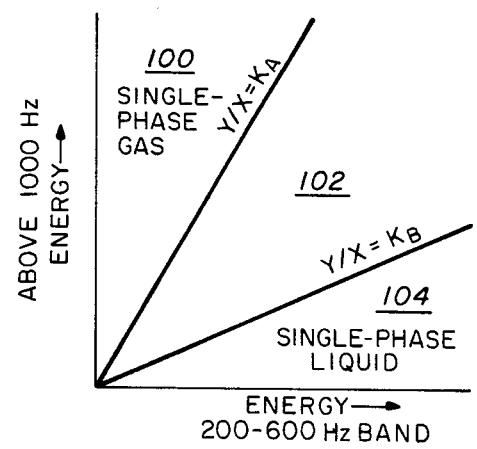
FIG. 3
FIG. 5
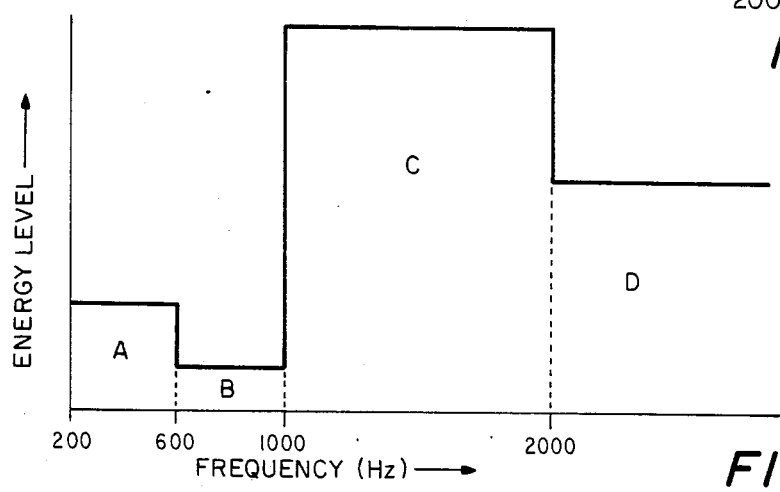
FIG. 4

METHOD AND APPARATUS FOR EVALUATING FLOW CHARACTERISTICS OF FLUID BEHIND PIPE

This application is a continuation, of application Ser. No. 436,235, filed Oct. 25, 1982, abandoned.

BACKGROUND OF THE INVENTION

This invention relates generally to methods and apparatus for evaluation of fluid flow characteristics and, more specifically, relates to acoustic well logging methods and apparatus for evaluation of flow characteristics of fluid behind subsurface casing or pipe.

When an earth borehole is drilled for the purpose of producing oil, gas, or other fluids, it is common practice to insert casing in the borehole before the production begins. To set the casing cement is pumped into the irregular annulus between the casing and the earth formations. Optimally, the cement bonds both to the casing and to the formations, thereby holding the casing securely in place and also isolating the different strata in the formations from one another. This isolation prevents the vertical migration of fluids from one strata to another and allows production to be obtained fom only those strata or zones desired. If the cement bonding is poor and has vertical fractures or channels, attempts to obtain production from the desired zones can be frustrated because less viscous or higher pressure liquids at other zones will flow vertically through the channel to the production zone. In this situation, hydrocarbon production will be at least substantially effected.

The fluids migrating through vertical channels can be either single-phase gas, single-phase liquid or some multi-phase combinations. The prior art has proposed several methods for locating vertical channels and monitoring fluid movement through these channels, for example U.S. Pat. No. 3,784,828, issued to D. A. Hayes and U.S. Pat. No. 4,173,718, issued to W. H. Fertl and assigned to the assignee of the present invention. However, prior art methods have not been successful in evaluating the nature of fluid flow in these channels; whether the flow is single-phase liquid, single-phase gas or some multi-phase mixture.

Accordingly, the present invention overcomes the deficiencies of the prior art by providing method and apparatus for evaluating the flow characteristics of fluids flowing within channels behind pipe or casing, more particularly for evaluating the flow characteristics of gas and liquid flowing within a channel behind pipe.

SUMMARY OF THE INVENTION

An elongated body member housing an acoustic transducer functioning as a microphone is positioned within a well in proximity to a channel located behind the casing. Acoustic energy resulting from flow through the channel is detected and coupled into signal processing circuitry. The acoustic energy is coupled into four high-pass filters which have cutoff frequencies of approximately 200 Hz, 600 Hz, 1000 Hz and 2000 Hz. The output signals from the filters are converted into D.C. signal levels indicating the energy levels of the respective signals. Further, the 200 Hz high-pass signal and the 600 Hz high-pass signal are processed to derive a band-pass signal corresponding to the acoustic energy within the 200–600 Hz band. The energy level of the 200–600 Hz band-pass is compared to the energy level of the 1000 Hz high-pass to provide an indicator of the flow characteristics of the fluid through the channel.

BRIEF DESCRIPTION OF THE DRAWINGS

FIG. 1 is a side elevation, partly in cross section, of a borehole logging instrument in operative position and the associated surface circuitry and related equipment.

FIG. 3 illustrates graphically the responsive curves corresponding to the output signals from the high-pass filter circuits of the electronic circuitry shown in FIG. 2.

FIG. 4 is a graphic representation of the energy level verses frequency of the acoustic data measured with the well logging instrument of the present invention.

FIG. 5 illustrates graphically the relative disbursement of acoustic energy between selected frequency ranges.

DETAILED DESCRIPTION OF THE PREFERRED EMBODIMENT

Figure 2:
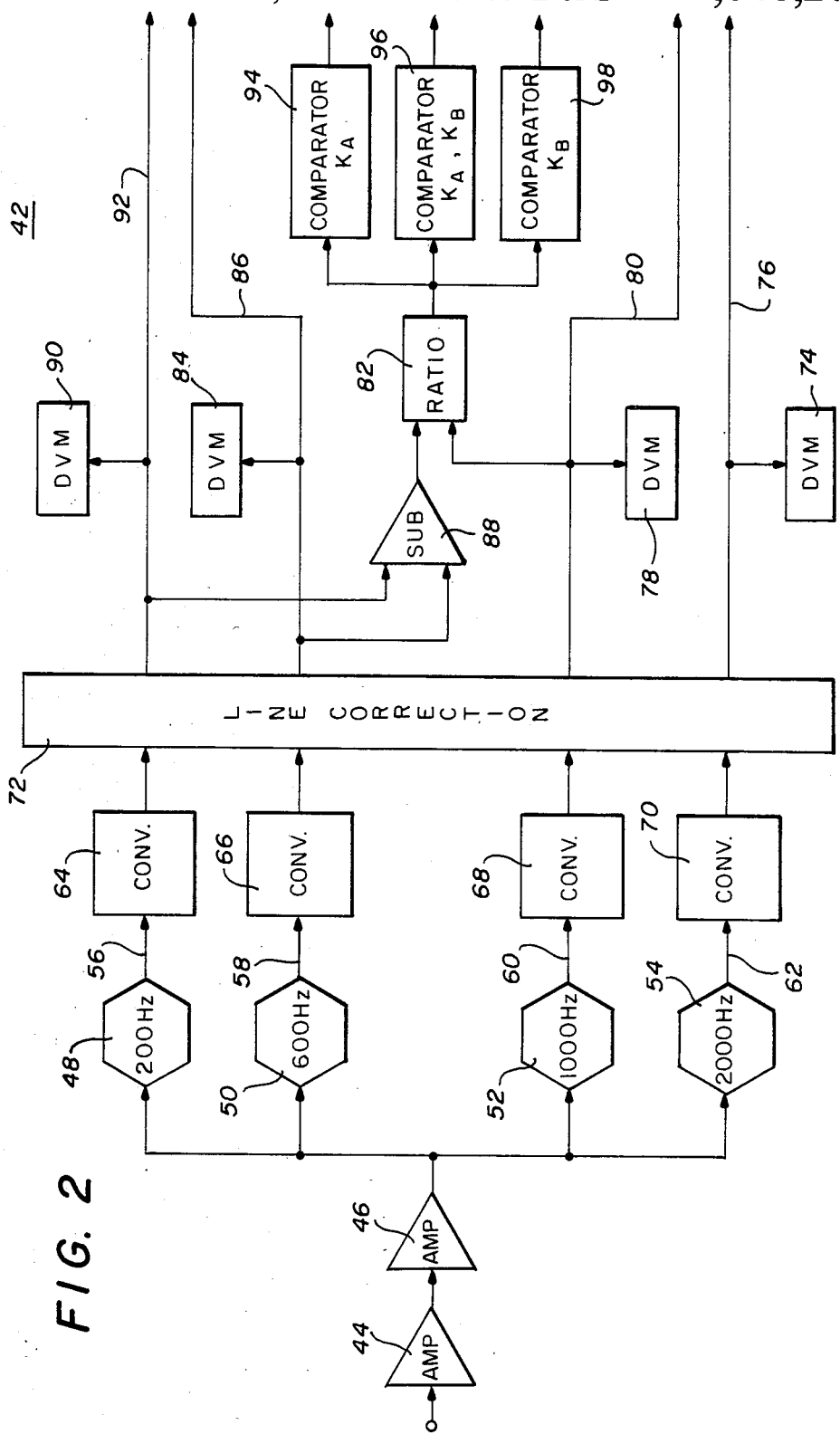
FIG. 2 illustrates representative electronic circuitry used with the well logging instrument in accordance with the present invention.

Referring now to the drawings in more detail, particularly to FIG. 1, therein is illustrated schematically a well logging operation in which a portion of the earth 10 is shown in vertical section. A well 12 penetrates the earth's surface wherein casing 14 has been installed and cement 16 pumped into the annulus between earth formations 10 and casing 14. Disposed within well 12 is subsurface instrument 18 of the well logging system.

Subsurface instrument 18 includes an electromechanical acoustic transducer 20 for detecting acoustic energy caused by fluid movement within and in the vicinity of well 12. Acoustic transducer 20 consists preferably of a plurality of piezoelectric transducers functioning as a microphone. Transducer 20 is electrically coupled to amplifier circuit 22 which is further electrically coupled to line driver circuit 24. The output signal from line driver circuit 24 is electrically coupled to electrical conductors within cable 26 for transfer to the surface electronics. Additionally, cable 26 suspends instrument 18 in well 12. Cable 26 is wound or unwound from drum 27 in raising and lowering instrument 18 to traverse well 12.

Disposed adjacent instrument 18 is an illustrative portion of the earth formations. The portion of the earth formations under consideration comprises three strata; a porous zone 28, such as a sand, which is bedded above by a relatively non-porous zone 30, such as a shale, and a topmost porous zone 32, such as a sand. Vertical fracture or channel 34 is illustrated as allowing fluid communication between porous zones 28 and 32. As previously stated this fluid can comprise single-phase gas, single-phase liquid or some multi-phase combination thereof.

Cable 26 passes over measuring wheel 36 which is electrically coupled to depth indicator circuit 38. The output signal from depth indicator circuit 38 is coupled into recorder 40 causing recorder 40 to move in correlation with depth as instrument 18 is positioned within well 12. The electrical signals from cable 26 are coupled by slip rings located on drum 27 into signal processor 42 where these electrical signals are processed and further coupled to recorder 40.

In the operation in accordance with the present invention, subsurface instrument 18 is positioned within well 12, disposed preferably proximate a channel, such as 34, fluidly communicating two strata 28 and 32. The acoustic patterns associated with fluid movement through channel 34 are detected by transducer 20 and coupled into amplifier circuit 22 where they are amplified before being coupled into line driver circuit 24. Line driver circuit 24 couples the electrical signals through conductors within cable 26 into signal processor 42.

Referring now to FIG. 2, therein is illustrated in greater detail a portion of the circuitry of signal processor 42. The output signals from line driver circuit 24 are coupled into first amplifier circuit 44 which functions as a signal conditioning amplifier. The output of amplifier 44 is coupled into second amplifier circuit 46, which in the preferred embodiment functions as a scaling amplifier having a fixed gain of 2.83. Scaling amplifier 46 converts the RMS input value to a peak-to-peak value. The output of amplifier 46 is parallel coupled into the inputs of four high-pass filters 48, 50, 52 and 54. High-pass filters 48, 50, 52 and 54 tramsmit all frequencies above individual preselected cutoff frequencies and substantially attenuate all other frequencies. In the preferred embodiment filter 48 has a cutoff frequency of approximately 200 Hz, filter 50 has a cutoff frequency of approximately 600 Hz, filter 52 has a cutoff frequency of approximately 1000 Hz and filter 54 has a cutoff frequency of approximately 2000 Hz. The outputs of filters 48, 50, 52 and 54 are illustrated in FIG. 3 with curve 56 representing the output signal from filter 48, curve 58 representing the output from filter 50, curve 60 representing the output from filter 52 and curve 62 representing the output from filter 54. The area A under the filter response curves represents the amount of acoustic energy that is concentrated in the frequency band from approximately 200–600 Hz; B the energy in the frequency band from approximately 600–1000 Hz; C the energy in the frequency band from approximately 1000–2000 Hz; and D the energy above approximately 2000 Hz. These energy concentrations are further illustrated in FIG. 4 which is an exemplary plot of energy level verses frequency.

The output signals from filters 48, 50, 52 and 54 are coupled into RMS-DC converters 64, 66, 68 and 70, respectively. The outputs are D.C. voltages which are the RMS values of the alternating voltage inputs thereto. Since the input signals have been multiplied by 2.83 by amplifier 46, the D.C. voltage outputs are the peak-to-peak value of the input signal to signal processor 42. These D.C. voltage outputs from converters 64, 66, 68 and 70 are coupled into line correction circuitry 72 wherein these input signals are corrected for line effects in a manner common in the art of well logging.

The 2000 Hz high-pass output, 62 of FIG. 3, from line correction circuit 72 is parallel coupled to digital volt meter 74 and to recorder 40 by conductor 76. The 1000 Hz high-pass output, 60 of FIG. 3, from line correction circuit 72 is coupled to digital volt meter 78 and to recorder 40 by conductor 80. Additionally, the 1000 Hz high-pass output is coupled into one input to ratio circuit 82. The 600 Hz high-pass output, 58 of FIG. 3, from line correction circuit 72 is parallel coupled to digital volt meter 84 and to recorder 40 by conductor 86. Additionally, the 600 Hz high-pass output is coupled into one input to subtractor circuit 88. The 200 Hz high-pass output, 56 of FIG. 3, from line correction circuit 72 is parallel coupled to digital volt meter 90 and recorder 40 by conductor 92. Additionally, the 200 Hz high-pass output is coupled into the second input to subtractor circuit 88. The output of subtractor circuit 88 is coupled into the second input to ratio circuit 82 the output of which is parallel coupled into the inputs to comparator circuits 94, 96 and 98, the outputs of which are coupled to recorder 40.

In the operation of the processing circuitry of FIG. 2, the composite acoustic data detected by transducer 20 (FIG. 1) is serially coupled through amplifier circuits 44 and 46. The amplified output from amplifier circuit 46 is parallel coupled into filters 48, 50, 52 and 54, which as previously stated are high-pass filters passing frequencies above a preselected cutoff frequencies. The output signals from high-pass filters (FIG. 3) are converted to D.C. level signals by converters 64, 66, 68 and 70 and corrected for line effects in line correction circuit 72. The 200 Hz high-pass output, 56 of FIG. 3, and the 600 Hz high-pass output, 58 of FIG. 3, are coupled into subtractor circuit 88. The output of subtractor 88 is a signal of the acoustic energy level within the frequency band from between 200–600 Hz, illustrated by area A of FIGS. 3 and 4. The output of subtractor circuit 88 is coupled into one input of ratio circuit 82 the other input being the acoustic energy level of the 1000 Hz high-pass range, curve 60 of FIG. 3 and the combination of areas C and D of FIG. 4. The output of ratio circuit 82 is an indication of the relative distribution of acoustic energy between the two selected frequency ranges. For illustrative purposes, the ratio output of ratio circuit 82 is parallel coupled into three comparator circuits 94, 96 and 98 where the signal is compared to the predetermined functions $K_A$ and $K_B$.

The operation of comparators 94, 96 and 98 is illustrated in FIG. 5 where energy level of the signal above 1000 Hz is shown on the ordinate, Y axis, and the energy level of the signal within the 200–600 Hz range is shown on the abscissa, X axis. Predetermined functions $K_A$ and $K_B$ divide the graph into three sectors, 100, 102 and 104. If the comparison of the energy distribution between the two preselected frequency bands yields a signal greater than the function $K_A$, then comparator circuit 94 outputs a signal. An output from comparator 94 is the functional equivalent of a ratio value located above $K_A$ in sector 100 of FIG. 5, and is indicative of single-phase gas flow within the channel. If the output signal from ratio circuit 82 is of a value less than $K_A$ but greater than $K_B$ comparator circuit 96 will output a signal. An output from comparator 96 is the functional equivalent of ratio value located in sector 102 of FIG. 5, and is assumed to be indicative of multi-phase flow or bubbling gas. (If the output signal from ratio circuit 82 is of a value less than $K_B$ comparator circuit 98 will output a signal. An output from comparator 98 is the functional equivalent of a ratio value located in sector 104 of FIG. 5, and is indicative of single-phase liquid flow.) Thus by monitoring the relative disbursement of acoustic energy between two selected energy ranges a reliable indicator of the characteristic of fluid flowing within a channel located behind pipe can be obtained. It should be recognized that the particular values for functions $K_A$ and $K_B$ are established through standard experimental techniques and in the preferred embodiment are approximately 2 and $\frac{1}{2}$, respectively.

Thus there has been described and illustrated herein a method and system in accordance with the present invention for evaluating the flow characteristics of fluid in channels located behind a pipe. Those skilled in the art will recognize that numerous other variations and modifications may be made without departing from the scope of the present invention. For example, the energy level signals corresponding to the selected energy bands could be plotted directly as Cartesian coordinates by means of an X-Y plotter, thus eliminating the need for a ratio signal. Accordingly, it should be clearly understood that the forms of the invention described and illustrated herein are exemplary only, and are not intended as limitations on the scope of the present invention.

The embodiments of the invention in which an exclusive property or privlege is claimed are defined as follows:

1. A method of qualitatively evaluating the nature of the phase of fluid flow within a vertical channel behind a pipe traversing earth formations to determine if said fluid flow is single-phase gas, single-phase liquid or a multi-phase combination flow, comprising the steps of:

measuring the acoustic energy resulting from said flow of fluid within a channel behind said pipe;

separating said measured acoustic energy into a plurality of frequency groups;

comparing the acoustic energy of a first frequency group, said first group consisting essentially of measured acoustic energy having frequencies within the range from approximately 200–600 Hz, to a second frequency group, said second group consisting essentially of measured acoustic energy having frequencies above approximately 1000 Hz, to determine a ratio of acoustic energy between said frequency groups; and producing a signal in response to said ratio indicative of the nature of said fluid flow indicating if said flow is single-phase gas, single-phase liquid or a multi-phase combination flow.

2. The method of claim 1, further comprising the step of comparing said acoustic energy of said first frequency group to said second frequency group to produce a ratio, wherein single-phase gas flow is indicated by a ratio of two or above of said acoustic energy in said second frequency group to said acoustic energy in said first frequency group.

3. The method of claim 2, further comprising the step of comparing said acoustic energy of said first frequency group to said second frequency group to produce a ratio, wherein single-phase liquid flow is indicated by a ratio of one half or less of said acoustic energy in said second frequency group to said acoustic energy in said first frequency group.

4. The method of claim 3 wherein said fluid flow is classified as a multi-phase combination flow when said ratio is less than two and more than one-half.

* * * * *